US00PP19092P2

(12) United States Plant Patent
Verduin

(10) Patent No.: US PP19,092 P2
(45) Date of Patent: Aug. 12, 2008

(54) ***ASTILBE* PLANT NAMED 'DIAMONDS AND PEARLS'**

(50) Latin Name: *Astilbe Chinensis*
Varietal Denomination: Diamonds and pearls

(75) Inventor: Henricus Gijsbertus Johannes Verduin, Heemskerk (NL)

(73) Assignee: Witteman & Co., Hillegom (NL)

( * ) Notice: Subject to any disclaimer, the term of this patent is extended or adjusted under 35 U.S.C. 154(b) by 0 days.

(21) Appl. No.: 11/728,162

(22) Filed: Mar. 23, 2007

(51) Int. Cl.
*A01H 5/00* (2006.01)

(52) U.S. Cl. ..... Plt./407; Plt./263
(58) Field of Classification Search ..... Plt./407, Plt./263
See application file for complete search history.

*Primary Examiner*—Kent L Bell
*Assistant Examiner*—S. B. McCormick-Ewoldt
(74) *Attorney, Agent, or Firm*—C. A. Whealy

(57) ABSTRACT

A new and distinct cultivar of *Astilbe* plant named 'Diamonds and Pearls', characterized by its upright and sturdy plant habit; strong and healthy foliage; freely and uniformly flowering habit; large white-colored flowers; and good garden performance.

3 Drawing Sheets

Botanical designation: *Astilbe chinensis.*
Cultivar denomination: 'Diamonds and Pearls'.

BACKGROUND OF THE INVENTION

The present invention relates to a new and distinct cultivar of *Astilbe,* botanically known as *Astilbe chinensis* and hereinafter referred to by the name 'Diamonds and Pearls'.

The new *Astilbe* is a product of a planned breeding program conducted by the Inventor in Heemskerk, The Netherlands. The objective of the breeding program was to create new *Astilbe* cultivars with healthy foliage and attractive flower coloration.

The new *Astilbe* originated from a cross-pollination made by the Inventor in 1998 in Heemskerk, The Netherlands, of two unidentified selections of *Astilbe chinensis,* not patented. The new *Astilbe* was discovered and selected by the Inventor as a single flowering plant within the progeny of the stated cross-pollination in a controlled environment in Heemskerk, The Netherlands in July, 1999.

Asexual reproduction of the new *Astilbe* by divisions in a controlled environment in Heemskerk, The Netherlands since January, 2000, has shown that the unique features of this new *Astilbe* are stable and reproduced true to type in successive generations.

SUMMARY OF THE INVENTION

The cultivar Diamonds and Pearls has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Diamonds and Pearls'. These characteristics in combination distinguish 'Diamonds and Pearls' as a new and distinct cultivar of *Astilbe:*

1. Upright and sturdy plant habit.
2. Strong and healthy foliage.

3. Freely and uniformly flowering habit.
4. Large white-colored flowers.
5. Good garden performance.

Plants of the new *Astilbe* and the parent selections differ primarily in flower coloration and plant height.

Plants of the new *Astilbe* can be compared to plants of the cultivar Diamant, not patented. In side-by-side comparisons conducted in Heemskerk, The Netherlands, plants of the new *Astilbe* and the cultivar Diamond differed in the following characteristics:

1. Plants of the new *Astilbe* were more compact than plants of the cultivar Diamant.
2. Plants of the new *Astilbe* were sturdier and had thicker stems than plants of the cultivar Diamant.
3. Plants of the new *Astilbe* had larger and fuller inflorescences than plants of the cultivar Diamant.
4. Plants of the new *Astilbe* had white-colored flowers whereas plants of the cultivar Diamant had greyish white-colored flowers.

Plants of the new *Astilbe* can also be compared to plants of the cultivar Milk and Honey, not patented. In side-by-side comparisons conducted in Heemskerk. The Netherlands, plants of the new *Astilbe* and the cultivar Milk and Honey differed in the following characteristics:

1. Plants of the new *Astilbe* were more compact than plants of the cultivar Milk and Honey.
2. Plants of the new *Astilbe* were sturdier than plants of the cultivar Milk and Honey.
3. Plants of the new *Astilbe* had darker green-colored foliage than plants of the cultivar Milk and Honey.
4. Plants of the new *Astilbe* had larger flowers than plants of the cultivar Milk and Honey.
5. Plants of the new *Astilbe* had white-colored flowers whereas plants of the cultivar Milk and Honey had pinkish white-colored flowers.

BRIEF DESCRIPTION OF THE PHOTOGRAPHS

The accompanying colored photographs illustrate the overall appearance of the new *Astilbe,* showing the colors as true as it is reasonably possible to obtain in colored reproductions of this type. Colors in the photographs may differ slightly from the color values cited in the detailed botanical description which accurately describe the colors of the new *Astilbe*.

The photograph on the first sheet comprises a side perspective view of a typical flowering plant of 'Diamonds and Pearls' grown in a container.

The photograph on the second sheet is a close-up view of typical inflorescences of 'Diamonds and Pearls'.

The photograph at the top of the third sheet is a close-up view of a typical inflorescence of 'Diamond and Pearls'.

The photograph at the bottom of the third sheet is a close-up view of the upper surface of a typical leaf of 'Diamonds and Pearls'.

DETAILED BOTANICAL DESCRIPTION

The aforementioned photographs and following observations, measurements and values describe plants grown in containers in Heemskerk, The Netherlands, under commercial practice during the late summer in an outdoor nursery with day temperatures ranging from 12° C. to 35° C. and night temperatures ranging from 12° C. to 18° C. Plants had been growing for about one year when the photographs and description were taken. In the following description, color references are made to The Royal Horticultural Society Colour Chart, 2001 Edition, except where general terms of ordinary dictionary significance are used.

Botanical classification: *Astilbe chinensis* cultivar Diamonds and Pearls.

Parentage:

*Female, or seed, parent.*—Unidentified selection of *Astilbe chinensis,* not patented.

*Male, or pollen, parent.*—Unidentified selection of *Astilbe chinensis,* not patented.

Propagation:

*Type.*—By divisions.

*Time to initiate roots.*—About 20 days at 15° C.

*Time to produce a rooted plant.*—About 50 days at 20° C.

*Root description.*—Fine; white in color.

*Rooting habit.*—Freely branching.

Plant description:

*Plant form/habit.*—Herbaceous perennial. Upright and sturdy plant habit; roughly triangular. Flowering stems and leaves basal; dense and bushy growth habit; moderately vigorous to vigorous growth habit. Freely and uniformly flowering with numerous flowers on branched panicles.

*Growth rate.*—Moderate to fast; from divisions, about 18 weeks are required to produce fully-grown flowering plants.

*Plant height* (*soil level to top of foliage plane*).—About 40 cm.

*Plant height* (*soil level to top of inflorescences*).—About 73 cm.

*Plant width* (*spread*).—About 68 cm.

*Stem description.*—Length: About 41.9 cm. Diameter: About 4 mm. Internode length: About 9.6 cm. Strength: Strong. Texture: Sparsely pubescent. Color: 144A.

Foliage description:

*Arrangement.*—Alternate; biternately compound.

*Leaf length* (*excluding petiole*).—About 23 cm.

*Leaf width.*—About 25.3 cm.

*Lateral leaflet length.*—About 4.4 cm.

*Lateral leaflet width.*—About 2.3 cm.

*Terminal leaflet length.*—About 5.8 cm.

*Terminal leaflet width.*—About 3.2 cm.

*Lateral leaflet shape.*—Narrowly ovate to elliptic.

*Terminal leaflet shape.*—Elliptic.

*Lateral and terminal leaflet apex.*—Acute.

*Lateral and terminal leaflet base.*—Attenuate.

*Lateral and terminal leaflet margin.*—Biserrate.

*Lateral and terminal leaflet texture, upper and lower surfaces.*—Sparsely pubescent; slightly rough.

*Lateral and terminal leaflet venation pattern.*—Pinnate.

*Lateral and terminal leaflet color.*—Developing leaves, upper surface: 137B. Developing leaves, lower surface: 138A. Fully expanded leaves, upper surface: 137A; venation, 143B. Fully expanded leaves, lower surface: 137B to 137C; venation, between 143C and 144A.

*Leaf petiole length.*—About 17.9 cm.

*Leaf petiole diameter.*—About 2.5 mm.

*Leaflet petiole length.*—About 6.1 cm.

*Leaflet petiole width.*—About 2.5 mm.

*Leaf and leaflet petiole texture, upper and lower surfaces.*—Smooth, glabrous.

*Leaf and leaflet petiole color, upper and lower surfaces.*—144A.

Flower description:

*Flower type/habit.*—Numerous single rotate flowers arranged on branches panicles; flowers fact upright, outward or downward depending on position on the panicle. Panicles conical in shape. Freely and uniformly flowering habit with about 1,500 flower buds and flowers developing per inflorescence; typically eight panicles develop per plant.

*Fragrance.*—Faintly fragrant; sweet.

*Natural flowering season.*—Continuously flowering during the summer in Heemskerk, The Netherlands.

*Postproduction longevity.*—Flowers last about ten days on the plant. Flowers persistent.

*Flower buds.*—Height: About 2.5 mm. Diameter: About 1.5 mm. Shape: Ovoid. Color: Between 155D and 158D.

*Inflorescence height.*—About 31.1 cm.

*Inflorescence diameter.*—About 11.9 cm.

*Flower diameter.*—About 1 cm.

*Flower depth.*—About 5 mm.

*Petals.*—Quantity per flower: Typically five in a single whorl. Length: About 6 mm. Lobe width: About 1 mm. Shape: Narrowly oblanceolate. Apex: Acute. Margin: Entire. Texture, upper and lower surfaces: Smooth, glabrous. Color: Developing petals, upper and lower surfaces: Close to 155D. Fully expanded petals, upper and lower surfaces: Close to 155D; color becoming closer to 157C to 157D with development.

*Sepals.*—Quantity per flower: Typically five in a single whorl, fused towards the base; campanulate calyx. Length: About 2 mm. Width: About 1 mm. Shape: Ovate. Apex: Acute. Margin: Entire. Texture, upper and lower surfaces: Smooth, glabrous. Color, developing sepals, upper and lower surfaces: Between 155D and 158D. Color, fully expanded sepals, upper and lower surfaces: 193A.

*Peduncles.*—Length: About 30.6 cm. Diameter: About 3 mm. Angle: Erect. Strength: Strong. Texture:

Smooth, glabrous. Color: 145C; towards the base, 144A; towards the apex, between 155D and 158D.

*Pedicels.*—Length: About 7.5 mm. Diameter: About 0.5 mm. Angle: About 45° from vertical. Strength: Moderately strong. Texture: Smooth, glabrous. Color: 193A to between 155D to 158D.

*Reproductive organs.*—Stamens: Quantity per flower: Typically ten; anthers basifixed. Filament length: About 2.5 mm. Anther shape: Oblong. Anther length: About 0.2 mm. Anther color: 155A. Pollen amount: Scarce. Pollen color: 155D. Pistils: Quantity per flower: Two. Pistil length: About 1.8 mm. Stigma shape: Club-shaped. Stigma color: 155A. Style length: About 1.7 mm. Style color: 155A. Ovary color: 155A.

*Seed/fruit.*—Seed and fruit development have not been observed.

Diseases/pest resistance: Plants of the new *Astilbe* have not been noted to be resistant to pathogens and pests common to *Astilbe*.

Garden performance: Plants of the new *Astilbe* have been observed to have good garden performance and tolerate rain, wind and high temperatures of about 35° C. Plants of the new *Astilbe* have been observed to be hardy to USDA Zone 5.

It is claimed:

1. A new and distinct *Astilbe* plant named 'Diamonds and Pearls' as illustrated and described.

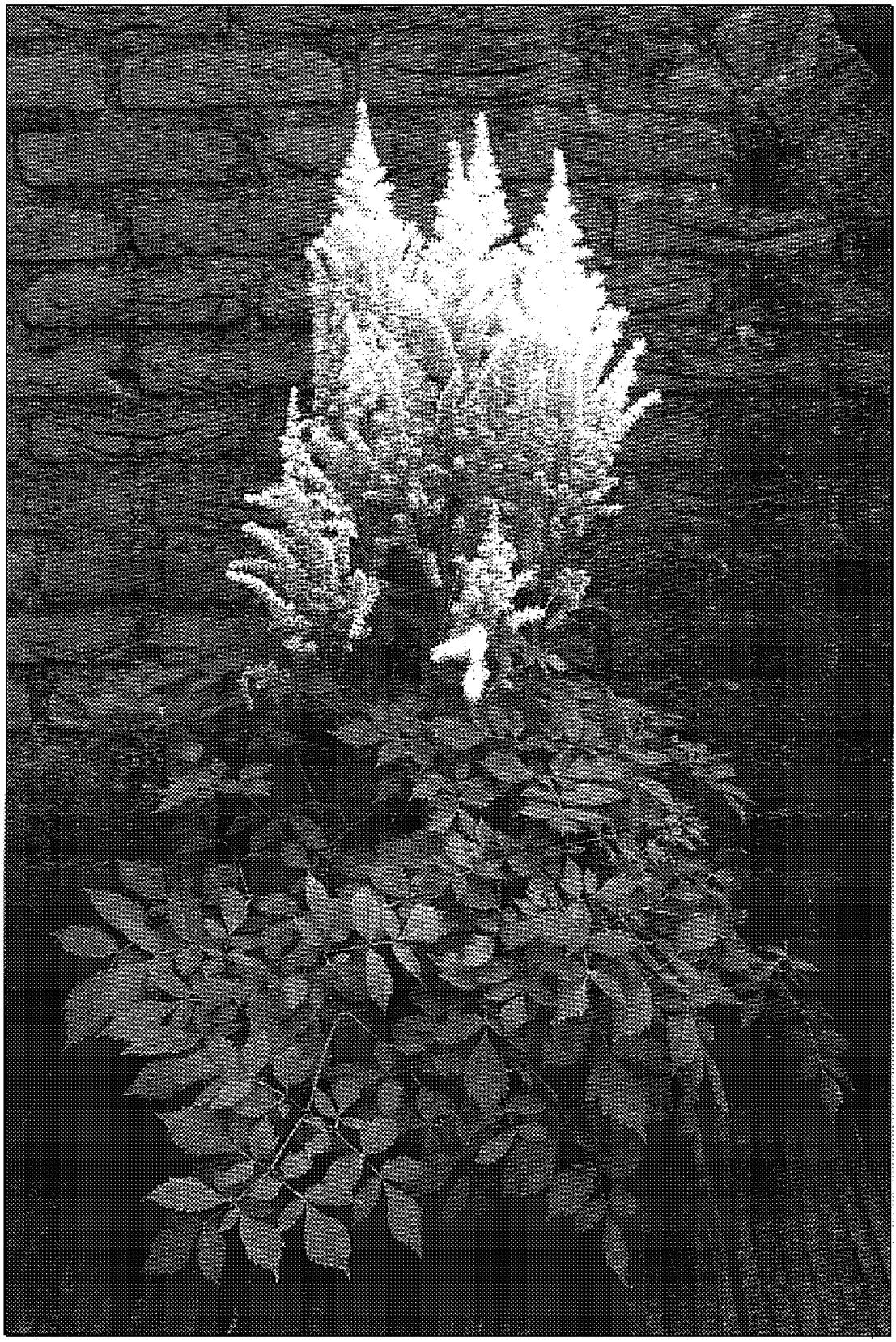

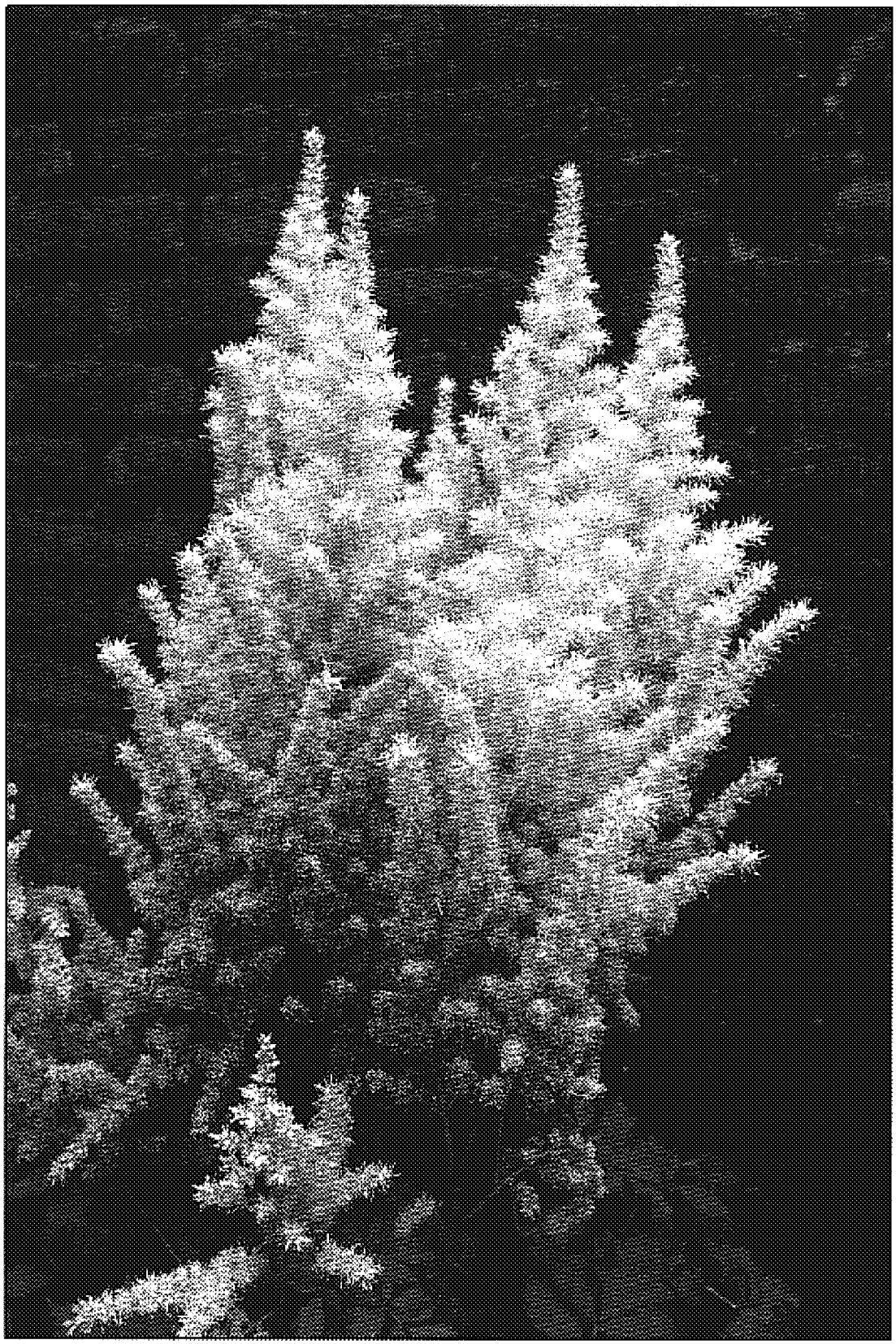

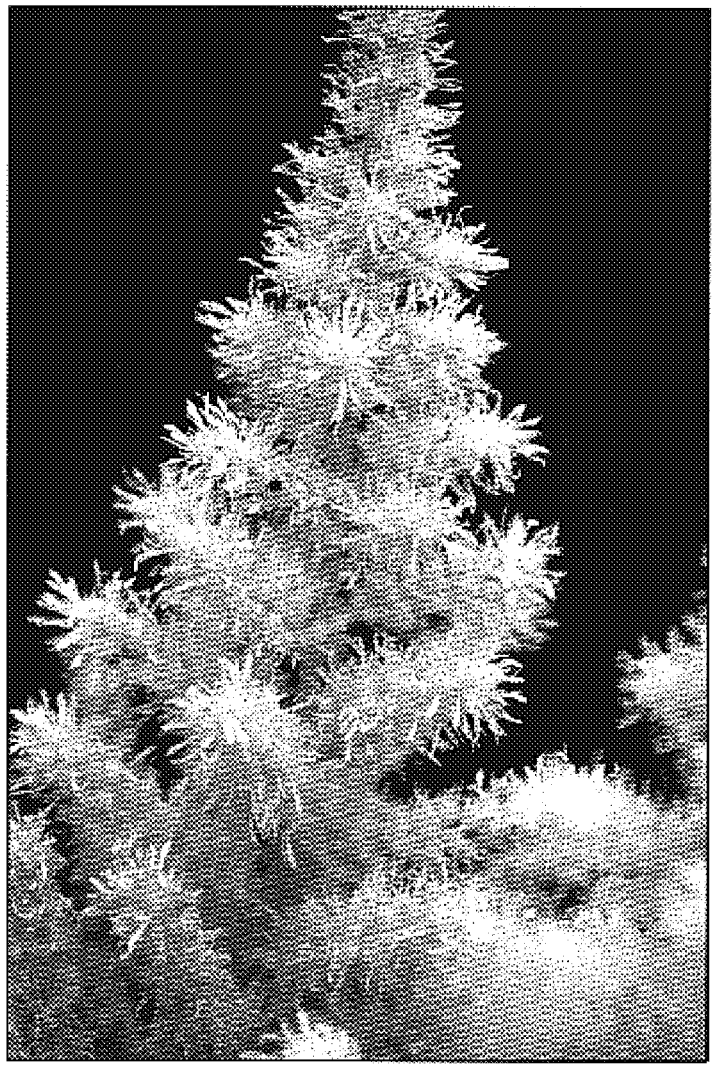
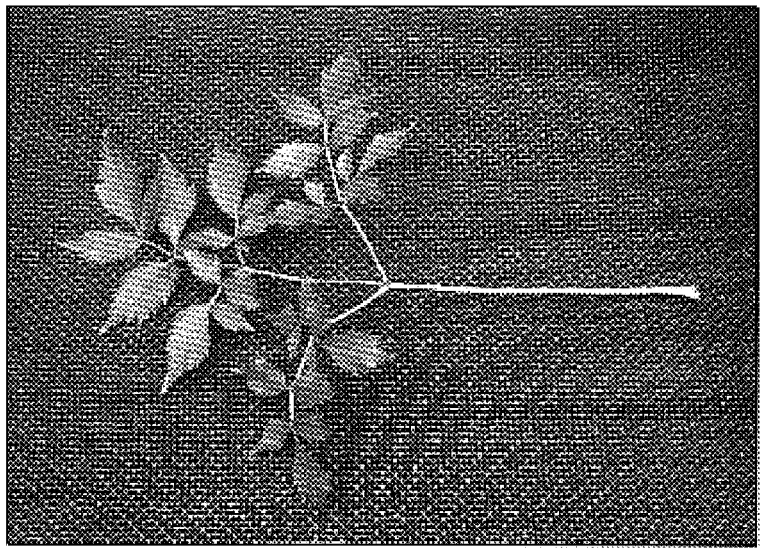

* * * * *